United States Patent [19]

Martinez et al.

[11] Patent Number: 5,605,976
[45] Date of Patent: Feb. 25, 1997

[54] METHOD OF PREPARING POLYALKYLENE OXIDE CARBOXYLIC ACIDS

[75] Inventors: Anthony J. Martinez, Hamilton Square; Richard B. Greenwald, Somerset, both of N.J.

[73] Assignee: Enzon, Inc., Piscataway, N.J.

[21] Appl. No.: 440,732

[22] Filed: May 15, 1995

[51] Int. Cl.$^6$ .................................................. C08G 65/32
[52] U.S. Cl. ...................... 525/408; 525/409; 528/300; 528/302; 528/361
[58] Field of Search .................. 525/408, 409; 528/300, 302, 361

[56] References Cited

U.S. PATENT DOCUMENTS

| | | | |
|---|---|---|---|
| 4,179,337 | 12/1979 | Davis et al. | 435/181 |
| 4,645,741 | 2/1987 | Inada | 435/134 |
| 4,760,176 | 7/1988 | Halpern et al. | 562/564 |
| 4,814,098 | 3/1989 | Inada et al. | 252/62.51 |
| 5,006,333 | 4/1991 | Saifer et al. | 424/78 |
| 5,122,614 | 6/1992 | Zalipsky | 548/520 |
| 5,183,660 | 2/1993 | Ikeda et al. | 424/94.3 |
| 5,298,643 | 3/1994 | Greenwald | 558/6 |
| 5,321,095 | 6/1994 | Greenwald | 525/404 |
| 5,349,001 | 9/1994 | Greenwald et al. | 525/408 |
| 5,389,381 | 2/1995 | Phillips et al. | 424/94.3 |

FOREIGN PATENT DOCUMENTS 9324476  12/1993  WIPO .

OTHER PUBLICATIONS

Chem. Abstracts 112:56926 Dal Pozzo et al.

Eur. Polym. J. vol. 19 No. 12, pp. 1177–1183 (1983), Zalipsky et al, "Attachment of Drugs to Polyethylene Glycols".

Biotechnology and Applied Biochemistry 9, 258–268 (1987), Buckmann et al, "Preparation of Technical Grade Polyethylene Glycol . . . ".

Journal of Controlled Release 10 (1989) 145–154 (1989), Veronese et al.

Advanced Drug Delivery Reviews 6 (1991) 133–151, Nucci et al, "The therapeutic value of Poly(ethylenglycol) Modified Proteins".

Cancer biochem. Biophys. (1964) vol. 7 pp. 175–186, Abuchowski et al, "Cancer Therapy . . . Conjugates".

Polymer Bulletin 18, 487–493 (1987), Gekehardt et al, "Soluble Polymers Organic Chemistry".

Journal of Polymer Science: Polymer Chemistry Edition, vol. 22 pp. 341–352 (1964), Harris et al, "Synthesis and Characterization of Poly(ethylene glycol) Derivatives".

Int. Arch Allergy Appl. Immun.64: 84–99 (1981), Wie et al., "Suppression of Reaginic Antibodies with Modified Allergens".

Primary Examiner—Melvyn I. Marquis
Assistant Examiner—Randy Gulakowski
Attorney, Agent, or Firm—Michael N. Mercanti

[57] ABSTRACT

The present invention is directed to methods of preparing high purity polyalkylene oxide carboxylic acids. The methods include reacting a polyalkylene oxide such as polyethylene glycol with a t-butyl haloacetate in the presence of a base followed by treatment with an acid such as trifluoroacetic acid. The resultant polymer carboxylic acids are of sufficient purity so that expensive and time consuming purification steps required for pharmaceutical grade polymers are avoided.

23 Claims, No Drawings

METHOD OF PREPARING POLYALKYLENE OXIDE CARBOXYLIC ACIDS

FIELD OF THE INVENTION

The present invention relates to methods of preparing activated polyalkylene oxides. In particular, the invention relates to methods of preparing polyalkylene oxide carboxylic acids in high purity.

BACKGROUND OF THE INVENTION

The conjugation of water-soluble polyalkylene oxides with therapeutic moieties such as proteins and polypeptides is known. See, for example, U.S. Pat. No. 4,179,337, the disclosure of which is hereby incorporated by reference. The '337 patent discloses that physiologically active polypeptides modified with PEG circulate for extended periods in vivo, have reduced immunogenicity and antigenicity.

To conjugate polyalkylene oxides, the hydroxyl endgroups of the polymer must first be converted into reactive functional groups. This process is frequently referred to as "activation" and the product is called an "activated polyalkylene oxide."

For the most part, research has been directed to covalent attachment of polyalkylene oxides (PAO's) to epsilon amino groups of proteins, enzymes and polypeptides. Covalent attachment of polyalkylene oxides to lysine amino groups has been effected by linking groups such as succinoyl-N-hydroxysuccinimide ester, as disclosed by Abuchowski et al., Cancer Biochem. Biophys., 7, 175–86 (1984), azlactones, aryl imidates and cyclic imide thiones. See U.S. Pat. Nos. 5,298,643, 5,321,095, and 5,349,001, for example. The contents of each of the foregoing patents are hereby incorporated by reference herein. PAO's have also been activated with hydrazine groups in order to couple the polymer to activated carbohydrate groups.

In addition to the foregoing, the conversion of terminal hydroxy groups of PAO's such as PEG to carboxylic acids has also been reported. PEG-acids are useful in at least two regards. First, carboxylic acid derivatives can be used directly to conjugate nucleophiles via available hydroxyl or amino moieties. Secondly, PAO carboxylic acids can be used as intermediates to form other types of activated polymers. For example, mPEG carboxylic acids can be converted to the succinimidyl ester derivative via N-hydroxysuccinimide and a condensing agent such as diisopropyl carbodiimide. Other activated PAO's can be prepared by reaction of the active ester with hydrazine to produce PAO-hydrazide derivatives.

The principal drawback in preparing carboxylic add derivative of polyalkylene oxides has been the difficulty in obtaining high yields of pure product. For example, *Journal of Controlled Release*, 10 (1989) 145–154 and *Polymer Bulletin*, 18, (1987), 487–493, describe the synthesis of mPEG acids by converting mPEG-OH to an ethyl ester followed by base catalyzed hydrolysis to form the carboxylic acid. Ostensibly, this classic approach should proceed without difficulty. In realty, however, this method at best provides m-PEG acids of about 90% purity, with the main product contaminant being the starting material, mPEG-OH. In addition, the separation of the desired PEG add from the starting PEG alcohol is very difficult. Standard laboratory methods such as fractional crystallization or column chromatography are not effective. *J. Polymer Sci. Polymer Chem. Ed.*, vol. 22, 341–352 (1984). Tedious column ion exchange or HPLC techniques provide purity of up to 95%, but these techniques are not suitable for large scale processes.

Preparation of a PEG-conjugated product, sometimes referred to as a pegylated product, using impure PEG carboxylic acids results in an mPEG-OH contaminated final product. For lower molecular weight peptides and organic conjugates, removal of the contaminant is very difficult due to the slight difference in molecular weight between the contaminant, mPEG-OH, and the desired polymer conjugate. In addition, using lower purity polymer-carboxylic acid derivatives necessarily reduce the yield of the desired conjugates while adding to manufacturing costs due to the need to undertake tedious and expensive separation steps.

A need exists, therefore, for an improved method of preparing high purity polyalkylene oxide carboxylic acids. The present invention addresses this need.

SUMMARY OF THE INVENTION

In one aspect, the present invention includes methods of preparing polyalkylene oxide carboxylic acids. The methods include reacting a polyalkylene oxide with a tertiary alkyl haloacetate in the presence of a base to form an intermediate tertiary alkyl ester of polyalkylene oxide carboxylic acid and thereafter reacting the intermediate tertiary alkyl ester with an acid such as trifluoroacetic acid to form a polyalkylene oxide carboxylic acid. This method advantageously provides material in high yield and purity.

Within this aspect of the invention, the preferred polyalkylene oxides include polyethylene glycol and omega-methoxy-polyethylene glycol. Preferred tertiary alkyl haloacetates include t-butyl bromo- or chloro-acetate as well as other tertiary alcohol esters of the haloacetic acid. The preferred bases used in the method include, for example, potassium t-butoxide, butyl lithium, and the like. The methods can be carried out using metal t-butoxides in an alcohol such as t-butanol or in other inert solvents such as toluene.

The methods of the present invention can be carried out using approximately equimolar ratios of tertiary alkyl haloacetate to polyalkylene oxide. It is preferred, however, that the tertiary alkyl haloacetate be present in an amount which is greater than the polyalkylene oxide on a molar basis.

In further aspects of the invention, there are provided methods of preparing high purity alpha and/or omega substituted polyalkylene oxides such as mono or bis-PEG-amines, PEG-amides and PEG-esters including the succinimidyl, methyl and ethyl esters. These aspects include converting the polyalkylene oxide carboxylic acids described above into the desired terminally substituted polymer. In yet a still further aspect of the invention, methods of preparing polyalkylene oxide-biologically active nucleophile conjugates are disclosed. In this aspect of the invention, the polyalkylene oxide carboxylic adds are reacted with a biologically-active nucleophile so that an ester linkage is formed between the polymer and the biologically-active nucleophile. For example, in this aspect of the invention, taxol-2'PEG-monoesters and 20-campthothecin PEG-esters can be prepared.

One of the chief advantages of the present invention is that the resulting polyalkylene oxide carboxylic acids are prepared in high purity. Thus, product contaminants, namely, the starting materials, such as m-PEG-OH are not found in appreciable amounts, that is, they are found in amounts of less than 8% and preferably less than 1% and most preferably less than 0.5%. As a remit, the separation of the desired carboxylic acid from the starting alcohol is not required. Furthermore, tedious column or ion exchange or HPLC techniques are not required to provide the desired carboxylic acid.

DETAILED DESCRIPTION OF THE INVENTION

1. Polymer Substituents and Polyalkylene Oxides

The carboxylic acid derivatives of the present invention are preferably prepared from poly(alkylene oxides) (PAO's) such as polyethylene glycol which are water soluble at room temperature. Within this group are omega-substituted polyalkylene oxide derivatives such as methoxypoly (ethylene glycols) (mPEG-OH). Other suitable alkyl-substituted PAO derivatives include those containing mono-terminal $C_1$–$C_4$ groups. Straight-chained non-antigenic polymers such as monomethyl PEG homopolymers are preferred. Alternative polyalkylene oxides such as other poly(ethylene glycol) homopolymers, other alkyl-poly(ethylene oxide) block copolymers, and copolymers of block copolymers of poly(alkylene oxides) are also useful. The polyalkylene oxides are preferably azeotroped prior to conversion to the carboxylic acid.

The polymers of the present invention have a molecular weight of between about 200 and about 100,000 daltons and preferably between about 2,000 and about 80,000 daltons. Molecular weights of between about 4,000 and about 50,000 daltons, however, are most preferred.

The method of the present invention can also be carried out with alternative polymeric substances such as dextrans or other similar non-immunogenic polymers that are capable of being functionalized or activated as mono- or bis- carboxylic acids. The foregoing is merely illustrative and not intended to restrict the type of non-antigenic polymers suitable for use herein.

2. Synthesis of the Carboxylic Acid Derivatives

The methods of the present invention for preparing a polyalkylene oxide carboxylic acid include:

i) reacting a polyalkylene oxide with a tertiary-alkyl haloacetate such as t-butyl haloacetate in the presence of a base to form a t-butyl ester of polyalkylene oxide carboxylic acid; and ii) reacting the t-butyl ester with an acid to form the polyalkylene oxide carboxylic acid.

An important aspect of the method of the present invention is that polyalkylene oxides can be readily converted into alpha and/or omega carboxylic acids by way of a tert-butyl ester intermediate with extremely high product purity levels. Polyalkylene oxides of various molecular weights, such as those set forth above in Section 1, can be converted into their respective anions with strong base and thereafter reacted with commercially-available tert-butyl haloacetates such as t-butyl bromoacetate to provide the tert-butyl ester in high yield. This intermediate can thereafter be rapidly converted in very high yields into the analogous carboxylic acid by use of an acid such as trifluoroacetic acid. The method is carded out at temperatures of from about 0° to about 50° C. Within this aspect of the invention, temperatures from about 10° to about 40° are preferred and temperatures of from about 20° to about 30° are especially preferred.

Suitable tertiary-alkyl haloacetates are of the formula:

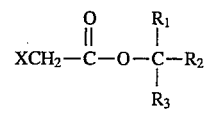

wherein

X is chlorine, bromine or iodine;

$R_{1-3}$ are independently selected from $C_{1-8}$ alkyls, substituted alkyls or branched alkyls, aryls such as phenyl or substituted phenyls.

Preferred t-butyl haloacetates include t-butyl bromoacetate, t-butyl chloroacetate, and t-butyl iodoacetate. Such t-butyl haloacetates are available, for example, from Sigma Chemical Co., St. Louis, Mo. Alternatively, trityl or substituted aryl esters can be used.

The first step of the preparation of the polyalkylene oxide carboxylic acids of the present invention includes forming an intermediate, t-butyl ester of polyalkylene oxide carboxylic acid. This intermediate is formed by reacting a polyalkylene oxide with a t-butyl haloacetate as described above in the presence of a base. The preferred base is potassium t-butoxide, although alternatives such as butyl lithium, sodium amide, or sodium hydride can also be used. Additional alternatives include sodium ethoxide and other strong bases. These bases can be used in the methods described herein as a solid, or more preferably, dissolved in a suitable solvent such as t-butanol, benzene, toluene, tetrahydrofuran (THF), dimethylformamide (DMF), dimethylsulfoxide (DMSO), hexane and the like.

In order to form the intermediate, the polyalkylene oxide is reacted with the t-butyl haloacetate in an amount which is approximately an equimolar ratio (1:1). Preferably, however, the t-butyl haloacetate is present in a molar excess so that complete conversion of the polyalkylene oxide is achieved. Thus, the molar ratio of t-butyl haloacetate to polyalkylene oxide is preferably greater than 1:1.

Once the t-butyl ester intermediate has been formed, the carboxylic acid derivative of the polyalkylene oxide can be readily provided in purities exceeding 92%, preferably exceeding 97%, more preferably exceeding 99% and most preferably exceeding 99.5% purity. Thus, contaminants, particularly with regard to the starting material e.g. mPEG-OH, are found in only trace amounts. In preferred aspects of the invention, where mono or bis-polyethylene glycol carboxylic acids are prepared, the amount of starting material contaminant found in the final product is less than 8%, preferably less than 3%, more preferably less than 1%, and most preferably in amounts of less than 0.5% by weight.

In this aspect of the invention, the t-butyl ester intermediate is reacted with at least an equivalent amount of an acid such as trifluoroacetic acid optionally in the presence of a small amount of water in order to provide the terminally substituted carboxylic acid of the PAO. Alternatively, dilute hydrochloric acid, i.e. about 1N, sulfuric, phosphoric acid, etc. can be used. The excess amount allows the artisan to convert the t-butyl ester intermediate to the desired carboxylic acid derivative and counteract the buffering capacity of PEG or related starting polymer material. Furthermore, the intermediate is preferably converted to the final carboxylic acid derivative in the presence of 3 to 5-fold molar excess of water based on the weight of the t-butyl ester intermediate and the reaction is carded out in an inert solvent such as methylene chloride, chloroform, ethyl acetate, etc.

The desired mono- or bis- carboxylic add derivative is obtained after allowing a sufficient time to assure conversion of the intermediate to the final acid derivative, which can be about 3 hours. The reaction time, however, will vary somewhat depending upon the particular reactants and reaction conditions. Furthermore, the reaction transforming the t-butyl intermediate into the desired carboxylic add can be carried out at room temperatures, i.e., 20°–30° C., although temperatures of from about 0° to about 50° C. may be used. After conversion of the intermediate to the final desired carboxylic acid, the solvent, i.e., methylene chloride, for example, is removed by distillation using techniques known to those of ordinary skill in the art such as rotary evaporation or the like. The resultant residue is recrystallized from methylene chloride/ethyl ether, toluene/ethyl ether or toluene/hexane to yield the final product.

After completion of the novel method, additional purification by conventional methods is not required since the methods described herein provide the desired carboxylic add in very high purity, i.e., preferably greater than 99%, thus providing the artisan with significant savings in terms of time, labor and materials when pharmaceutical grade polymer is desired.

3. Additional Alpha and/or Omega Terminal Moieties

As a further aspect of the invention, the mono- or bis-carboxylic acid derivatives can be used to form other activated polyalkylene oxides. For example, the terminal carboxylic acid group(s) can be converted to:

I. Functional groups capable of reacting with an amino group such as:
  a) succinimidyl ester;
  b) carbonyl imidazole;
  c) azlactones;
  d) cyclic imide thiones;
  e) isocyanates or isothiocyanates; or
  f) aldehydes II. Functional groups capable of reacting with carboxylic acid groups and reactive carbonyl groups such as:
  a) primary amines; or
  b) hydrazine and hydrazide functional groups such as the acyl hydrazides, carbazates, semicarbazates, thiocarbazates, etc.; or
  c) alcohols, i.e. those derived from ethyl esters.

The terminal activating group can also include a spacer moiety located proximal to the polyalkylene oxide. The spacer moiety may be a heteroalkyl, alkoxy, alkyl containing up to 18 carbon atoms or even an additional polymer chain. The spacer moieties can be added using standard synthesis techniques.

4 Conversion of the Carboxylic Acid Derivatives

The polymer carboxylic add derivatives also serve as high purity intermediates which can used to form additional polyalkylene oxide derivatives. For example, alpha and/or omega PEG-carboxylic acid derivatives can be converted into their respective PEG-amine derivatives by converting the PEG-carboxylic acid into an acid chloride intermediate before forming the amine by Hoffman degradation. Similarly, high purity amides, hydrazides, other esters and the like can be formed from the PAO carboxylic acid activated N-hydroxysuccinimide ester by condensing with the appropriate reagent (amides, hydrazines, etc.) using standard techniques.

Alternatively, the carboxylic acid derivative can be convened into a succinimidyl ester by reacting the carboxylic acid with dicyclohexyl carbodiimide (DCC) or diisopropyl carbodiimide in the presence of base.

These subsequent conversion reactions are essentially standard techniques well known to those of ordinary skill in the art. An important aspect of this feature of the invention is the fact that the intermediate, e.g. PEG-carboxylic acid is essentially pure (99+%) and thus assures the artisan of an essentially pure final product.

5. Biologically Active Materials Suitable for Conjugation

The nucleophiles conjugated with the carboxylic acid derivatives are described as "biologically active". The term, however, is not limited to physiological or pharmacological activities. For example, some nucleophile conjugates such as those containing enzymes, are able to catalyze reactions in organic solvents. Likewise, some inventive polymer conjugates are also useful as laboratory diagnostics. A key feature of all of the conjugates is that at least some portion of the activity associated with the unmodified biologically active material is maintained.

In accordance with the present invention, the nucleophile, having an available hydroxyl moiety capable of undergoing substitution without loss of bioactivity, is reacted with the carboxylic acid derivative of the polymer, such as PEG-COOH, under conditions sufficient to cause the formation of an ester linkage between the two substituents. As illustrative examples, taxol and taxotere conjugates are shown below:

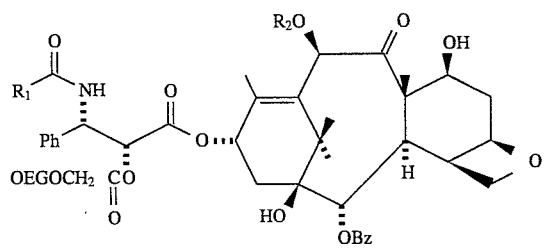

Protaxol: $R_1=C_6H_5$; $R_2=CH_3CO$

Protaxotere: $R_1=(CH_3)_3CO$; $R_2=H$

The corresponding diester can be prepared by reacting at least about 2 equivalents of the desired bioactive material per equivalent of PAO diacid. Details concerning formation of these conjugates is found in the Examples. For purpose of illustration, however, the conditions which are generally accepted as sufficient for allowing the ester linkage to form between non-protein or non-peptide agents and the polymer induce dissolving the polymer and target moiety in the suitable solvent system, i.e., methylene chloride at about room temperature, adding an acid activating agent such as DCC or diisopropyl carbodiimide and a base such as pyridine. Aqueous systems, on the other hand, will usually be required for target moieties capable of being denatured by organic systems.

In a further aspect of the invention, when the carboxylic acid has been converted to an alternative terminal functional group, such as a succinimidyl ester, conjugation of the activated polymer with the desired nucleophile is achieved by reacting the polymer with a biologically-active nucleophile containing an available amino group. See also, for example, U.S. Pat. No. 5,122,614, the disclosure of which is incorporated herein by reference. Similarly, when other linking groups such as those set forth above in Section 3, are used, PAO-conjugates can be prepared by reacting the desired activated polymer with a biologically-active material containing a desired target linking group, i.e., $NH_2$, COOH, etc. It is to be understood that the conditions used for completing these conjugation reactions are selected so as to maintain optimum biological activity of the conjugate.

The conjugates are biologically active and have numerous therapeutic applications. Mammals in need of treatment which includes a biologically active material can be treated by administering an effective amount of a polymer conjugate containing the desired bioactive material. For example, mammals in need of enzyme replacement therapy or blood factors can be given polymer conjugates containing the desired material. The doses of such conjugates are amounts which are sufficient to achieve a desired therapeutic result and will be apparent to those of ordinary skill based on clinical experience.

Biologically active nucleophiles of interest of the present invention include, but are not limited to, proteins, peptides, polypeptides, enzymes, organic molecules of natural and synthetic origin such as medicinal chemicals and the like.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubin oxidase. Carbohydrate-specific enzymes of interest include glucose oxidases, glucosidases, galactosidases, glucocerebrosidases, glucouronidases, etc.

Proteins, polypeptides and peptides of interest include, but are not limited to, hemoglobin, serum proteins such as blood factors including Factors VII, VIII, and IX; immunoglobulins, cytokines such as interleukins, $\alpha$-, $\beta$- and $\gamma$-interferons, colony stimulating factors including granulocyte colony stimulating factors, platelet derived growth factors and phospholipase-activating protein (PLAP). Other proteins of general biological or therapeutic interest include insulin, plant proteins such as lectins and ricins, tumor necrosis factors, growth factors, tissue growth factors, TGF$\alpha$'s or TGF$\beta$'s and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Some proteins such as the interleukins, interferons and colony stimulating factors also exist in non-glycosylated form, usually as a result of using recombinant techniques. The non-glycosylated versions are also among the biologically active nucleophiles of the present invention.

The biologically active nucleophiles of the present invention also include any portion of a polypeptide demonstrating in-vivo bioactivity. This includes amino acid sequences, antisense moieties and the like, antibody fragments, single chain antigen binding proteins, see, for example U.S. Pat. No. 4,946,778, disclosure of which is incorporated herein by reference, binding molecules including fusions of antibodies or fragments, polyclonal antibodies, monoclonal antibodies, catalytic antibodies, nucleotides and oligonucleotides.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained from transgenic animals, i.e., mice, pigs, cows, etc., wherein the proteins are expressed in milk, blood or tissues. Transgenic insects and baculovirus expression systems are also contemplated as sources. Moreover, mutant versions of proteins, such as mutant TNF's and mutant interferons are also within the scope of the invention.

Other proteins of interest are allergen proteins such as ragweed, Antigen E, honeybee venom, mite allergen, and the like.

Useful biologically active nucleophiles are not limited to proteins and peptides. Essentially any biologically-active compound is included within the scope of the present invention. Chemotherapeutic molecules such as pharmaceutical chemicals i.e. anti-tumor agents, cardiovascular agents, anti-neoplastics, anti-infectives, anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like are included. In preferred aspects of the invention, the carboxylic acid derivative is reacted under conditions which afford an ester linkage between the polymer and chemotherapeutic moiety. Particularly preferred biologically active nucleophiles include taxol, tames, taxotere, camptothecin, podophyllotoxin, hemoglobin, glucocerebrosidase, galactosidase, arginase, asparaginase, arginine deaminase and superoxide dismutase.

The foregoing is illustrative of the biologically active nucleophiles which are suitable for conjugation with the polymers of the invention. It is to be understood that those biologically active materials not specifically mentioned but having suitable nucleophilic groups are also intended and are within the scope of the present invention.

6. Synthesis of Biologically Active Conjugates

One or more of the polymer acids can be attached to a biologically active nucleophile by standard chemical reactions. The conjugate is represented by the formulae:

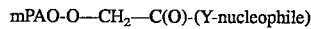

or

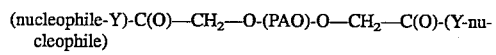

wherein:

PAO is a water-soluble polyalkylene oxide m is methyl; and

Y is N(L), O or S, where L is H, $C_{1-12}$ alkyl or aryl.

The upper limit of PAO's attached to the nucleophile is determined by the number of available attachment sites, i.e., hydroxyl moieties if the PAO acid is used, and the degree of polymer attachment sought by the artisan. The degree of conjugation can be modified by varying the reaction stoichiometry using well-known techniques. More than one polymer conjugated to the nucleophile can be obtained by reacting a stoichiometric excess of the activated polymer with the nucleophile.

The biologically active nucleophiles, such as enzymes, proteins and polypeptides, can be reacted with the activated polymers in an aqueous reaction medium which can be buffered, depending upon the pH requirements of the nucleophile. The optimum pH for the reaction is generally between about 6.5 and about 8.0 and preferably about 7.4 for proteinaceous/polypeptide materials. Organic/chemotherapeutic moieties are be reacted in non-aqueous systems. The optimum reaction conditions for the nucleophile's stability, reaction efficiency, etc. is within level of ordinary skill in the art. The preferred temperature range is between 4° C. and 37° C. The temperature of the reaction medium cannot exceed the temperature at which the nucleophile may denature or decompose. It is preferred that the nucleophile be reacted with an excess of the activated polymer. Following the reaction, the conjugate is recovered and purified such as by diafiltration, column chromatography, combinations thereof; or the like.

EXAMPLES

The following non-limiting examples illustrate certain aspects of the invention. All parts and percentages are by weight unless otherwise noted and all temperatures are in degrees Celsius.

Materials

Methoxypoly(ethylene glycol) (m-PEG-OH) MW 5,000 daltons was obtained from Union Carbide; PEG MW 20,000 and 40,000 daltons were obtained from Serva, Inc. The solvents were obtained from Aldrich Chemical of Milwaukee, Wis. Each of the products prepared in Examples 1–11 were confirmed structurally by carbon$^{13}$ NMR.

Example 1 t-Butyl Ester of m-PEG (5,000) Carboxylic Acid

A solution of 75 grams (0.015 moles) of m-pEG-OH in 750 ml of toluene was azeotroped with the removal of 150 ml of distillate. The reaction mixture was then cooled to 30° C., followed by the addition of 25 ml (0.025 moles) of a 1.0 molar solution potassium t-butoxide in t-butanol. The resulting mixture was stirred for 1 hour at room temperature, followed by the addition of 5.9 gram (0.030 moles) of t-butyl bromoacetate. The resulting cloudy mixture was heated to reflux, followed by removal of the heat, and stirring for 18 hours at room temperature. The reaction mixture was filtered through celite and the solvent removed by rotary evaporation. The residue was recrystallized from methylene chloride/ethyl ether to yield 75.9 grams (98% yield). The purity of the named product was determined by $^{13}$CNMR to be in excess of 99%; mPEG-OH <1.0%. $^{13}$CNMR assignments: ($\underline{C}H_3)_3C$, 27.6 ppm; $OCH_3$, 58.3 ppm; $(CH_3)_3\underline{C}$, 80.6 ppm; C=O, 168.9 ppm.

Example 2 m-PEG (5,000) Carboxylic Acid

A solution of 10.0 grams (2 mmoles) of m-PEG carboxylic acid t-butyl ester, 50 ml of trifluoracetic acid, and 0.1 ml of water in 100 ml of methylene chloride was stirred at room temperature for 3 hours. The solvent was then removed by rotary evaporation, followed by recrystallization of the residue from methylene chloride/ethyl ether to yield 9.4 grams (95% yield) of product. Purity of the desired product was determined to be in excess of 99%, mPEG-OH <1.0%. $^{13}$CNMR assignments: $OCH_3$, 58.3; C=O, 170.7 ppm.

Example 3 t-Butyl Ester of m-PEG (12,000) Carboxylic Acid

A solution of 50 grams (4.2 mmoles) of m-PEG-OH (12,000) in 750 ml of toluene was azeotroped with the removal of 150 ml of distillate. The reaction mixture was then cooled to 30° C., followed by the addition of 6.3 ml (6.3 mmoles) of a 1.0 molar solution of potassium t-butoxide in t-butanol. The resulting mixture was stirred for 1 hour at room temperature, followed by the addition of 2.3 grams (12.0 mmoles) of t-butylbromoacetate. The resulting cloudy mixture was heated to reflux, followed by removal of the heat, and stirring for 18 hours at room temperature. The reaction mixture was filtered through celite and the solvent removed by rotary evaporation. The residue was recrystallized from methylene chloride/ethyl ether to yield 41.2 grams (82% yield). The purity of the named product was determined by $^{13}$C NMR to be in excess of 99%; mPEG-OH <1.0%. $^{13}$CNMR assignments: ($\underline{C}H_3)_3C$, 27.5 ppm; OCH3, 58.4 ppm; $(CH_3)_3\underline{C}$, 80.7 ppm; C=O, 169.0 ppm.

Example 4 m-PEG (12,000) Carboxylic Acid

A solution of 10.0 grams (0.83 mmoles) of m-PEG (12,000) carboxylic acid t-butyl ester, 50 ml of trifluoroacetic acid, and 0.1 ml of water in 100 ml of methylene chloride was stirred at room temperature for 3 hours. The solvent was then removed by rotary evaporation, followed by trituration in ethyl ether to yield 9.75 grams (98% yield) of product. The purity of the named product was determined by $^{13}$CNMR to be in excess of 99%; mPEG-OH <1.0%. $^{13}$CNMR assignments: $OCH_3$, 58.3 ppm; C=O, 170.6 ppm.

Examples 5, 6 and 7

Following the procedures of Examples 3 and 4, m-PEG acids MW=2,000, 20,000 and 42,000 were also prepared. The respective products were found to be over 99% pure and were recovered in yields(from the alcohols) of 89% for the MW 2,000; 52% for the MW 20,000; and 76% for the MW 42,000.

Example 8

Di-t-Butyl Ester of PEG (40,000) Di-Carboxylic Acid

A solution of 50 grams (1.3 mmoles) of PEG-(OH)$_2$ in 750 ml of toluene was azeotroped with the removal of 150 ml of distillate. The reaction mixture was then cooled to 30° C., followed by the addition of 4 ml (4.0 mmoles) of a 1.0 molar solution of potassium t-butoxide in t-butanol. The resulting mixture was stirred for 1 hour at room temperature, followed by the addition of 1.6 grams (8.0 mmoles) of t-butylbromoacetate. The resulting cloudy mixture was heated to reflux, followed by removal of the heat, and stirring for 18 hours at room temperature. The reaction mixture was filtered through celite and the solvent removed by rotary evaporator. The residue was recrystallized from methylene chloride/ethyl ether to yield 45.2 grams (86% yield). The named product, however was found to be over 99% pure, the starting material being present in an amount of less than 1.0%. $^{13}$CNMR assignments: $(\underline{C}H_3)_3C$, 27.7 ppm; $(CH)_3\underline{C}$, 80.9 ppm; C=O, 169.1 ppm.

Example 9

PEG (40,000) Di-Carboxylic Acid

A solution of 20.0 grams (0.5 mmoles) of PEG (40,000) carboxylic acid t-butyl ester, 100 ml of trifluoroacetic acid, and 0.1 ml of water in 200 ml of methylene chloride was stirred at room temperature for 3 hours. The solvent was then removed by rotary evaporation, followed by recrystallization of the residue from methylene chloride/ethyl ether to yield 16.9 grams (84% yield) of product. Purity of the named product was confirmed to be in excess of 99%. $^{13}$CNMR assignments: C=O, 170.9 ppm.

Examples 10 and 11

Following the procedures of Examples 8 and 9, PEG di-acids of MW=6,000 and 35,000 were also prepared. The yields (from the alcohols) were determined to be 77% for the MW 6,000 derivative and 81% for the MW 35,000 derivative. In all cases, the purity of the final product was determined to be in excess of 99%.

Example 12—Comparative

In this example, samples of mPEG-COOH (MW 5,000) were prepared using the ethyl ester rather than the t-butyl derivative of the present invention in order to demonstrate the substantial differences in purity provided by the methods of the present invention. Percent purity was determined by $^{13}$CNMR.

Example 12(a)

Ethyl Ester of m-PEG (5,000) Carboxylic Acid

A solution of 10.0 g (2.0 mmoles) of m-PEG-OH in 150 ml of toluene was azeotroped with the removal of 75 ml of distillate. The reaction mixture was cooled to 40° C., followed by the addition of 0.6 g (5.0 mmoles) of potassium t-butoxide. The resulting mixture was stirred for 2 hours at 40° C., followed by the addition of 3.3 g (20 mmoles) of ethyl bromoacetate. The resulting solution was stirred for 18 hours at 40° C., followed by filtration through celite and removal of the solvent from the filtrate by rotary evaporation. The residue was recrystallized from 2-propanol to yield 7.2 g (71% yield). $^{13}$C NMR assignments: $CH_3CH_2$, 13.12 ppm; $(CH)_3O$, 57.83 ppm; $CH_3CH_2$, 59.47 ppm, C=O, 169.18 ppm Impurity: m-PEG-$CH_2$OH, 60.20 ppm.

Example 12(b)

m-PEG (5,000) Carboxylic Acid

A solution of 3.0 g (0.6 mmoles) of the ethyl ester of m-PEG (5,000) carboxylic acid from Example 12(a) and 0.2 g (5.0 mmoles) of sodium hydroxide in 25 ml of water was stirred for 18 hours at room temperature. The reaction mixture was then acidified with hydrochloric acid to pH 2.0, followed by extraction with methylene chloride. The combined extracts were dried over anhydrous sodium sulfate and filtered, followed by removal of the solvent from the filtrate by rotary evaporation. The residue was recrystallized from 2-propanol to yield 2.4 g (80% yield). $^{13}$C NMR assignments: $(CH)_3O$, 57.91 ppm; C=O, 170.30 ppm. Impurity: m-PEG-CH2OH, 60.50 ppm The average quantity of m-PEG-OH impurity found using standard literature preparations of m-PEG acid averages 17%. In eight procedures carried out using the above comparative techniques, the amount of impurities ranged from 9% to 31%. These results were then compared to the results obtained from the product of Example 2 (mPEG-COOH) and shown below.

COMPARATIVE TABLE

| METHOD | % PURITY |
| --- | --- |
| Ethyl ester (eight preparations) | 69–91 |
| t-butyl ester (Example 2) | 99+ |

As can be seen from the foregoing there are substantial advantages provided by synthesizing the carboxylic acid derivative using the t-butyl ester. It can also be seen that the ethyl ester derived PEG carboxylic acid requires further purification before it could be considered suitable for conjugation reactions with biologically active nucleophiles.

Example 13

Preparation of 20-Camptothecin PEG 5,000 Ester

The mPEG 5,000 acid (400 mg, 0.079 mmol) from Example 2 was azeotroped using toluene and then dissolved in 10 ml of anhydrous methylene chloride at room temperature and treated with 1,3-diisopropyl carbodiimide (18.1 μl, 0.119 mmol), 4-dimethylamino pyridine (14.5 mg, 0.119 mmol) and (S)-(+)-camptothecin (41.32 mg, 0.119 mmol) at 0° C. The reaction solution was warmed to room temperature over 30 minutes and kept at that temperature for 16 hours. The reaction solution was then washed with 0.1N HCl, dried and evaporated to yield an off-white solid which was purified by chromatography (silica gel, MeOH/$CH_2Cl_2$). The purified material was crystallized from $CH_2Cl_2$/ether.

Example 14

A. Taxol-2'PEG 5,000 Monoester Preparation

The mPEG 5,000 acid (625 mg, 0.125 mmol) from Example 2 was azeotroped and then dissolved in 20 ml of anhydrous methylene chloride at room temperature. The above solution was treated with 1,3-diisopropyl-carbodiimide (26 μl, 0.17 mmol), 4-dimethylaminopyridine (32 mg, 0.26 mmol) and taxol (146 mg, 0.17 mmol) at 0° C. The reaction solution was warmed to room temperature after 30 minutes and kept at that temperature for 16 hours. The reaction mixture was then washed with 0.1 n HCl, dried and evaporated to yield a white solid which was crystallized from 2-propanol to yield 585 mg (80% yield) of pure product.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

What is claimed is:

1. A method of preparing a polyalkylene oxide containing a terminal carboxylic acid, comprising:
   i) reacting a polyalkylene oxide with a tertiary alkyl haloacetate in the presence of a base to form a tertiary alkyl ester of polyalkylene oxide carboxylic acid; and
   ii) reacting said tertiary alkyl ester with an acid to form said polyalkylene oxide carboxylic acid.

2. The method of claim 1, wherein said polyalkylene oxide is polyethylene glycol.

3. The method of claim 2, wherein said polyethylene glycol is omega methoxypolyethylene glycol.

4. The method of claim 1, wherein said tertiary alkyl haloacetate comprises the formula:

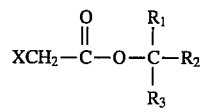

wherein

X is chlorine, bromine or iodine;

$R_{1-3}$ are independently selected from the group consisting of $C_{1-8}$ alkyls or $C_{1-8}$ branched alkyls and aryls.

5. The method of claim 4, wherein said tertiary alkyl haloacetate is a tertiary butyl haloacetate.

6. The method of claim 5, wherein said t-butyl haloacetate is t-butyl bromoacetate.

7. The method of claim 6, wherein said t-butyl haloacetate is t-butyl chloroacetate.

8. The method of claim 4, wherein $R_{1-3}$ are independently selected $C_{1-3}$ alkyls.

9. The method of claim 4, wherein $R_{1-3}$ are methyl.

10. The method of claim 1, wherein said base is potassium t-butoxide.

11. The method of claim 1, wherein said base is selected from the group consisting of butyl lithium, sodium amide and sodium hydride.

12. The method of claim 1, wherein the molar ratio of said t-butyl haloacetate to said polyalkylene oxide is greater than 1:1.

13. The method of claim 1, wherein said acid is trifluoroacetic acid.

14. The method of claim 1, wherein said acid is selected from the group consisting of sulfuric, phosphoric and hydrochloric acids.

15. The method of claim 1, wherein said reacting step ii) is carded out at a temperature of from about 0° to about 50° C.

16. The method of claim 15, wherein said reacting step ii) is carded out at a temperature of from about 20° to about 30° C.

17. The method of claim 1, wherein said reacting step ii) is carded out in the presence of water.

18. The method of claim 1, wherein said polyalkylene oxide has a molecular weight of from about 200 to about 100,000.

19. The method of claim 18, wherein said polyalkylene oxide has a molecular weight of from about 2,000 to about 80,000.

20. The method of claim 19, wherein said polyalkylene oxide has a molecular weight of from about 4,000 to about 50,000.

21. The method of claim 1, wherein the purity of said polyalkylene oxide carboxylic acid is greater than 92%.

22. The method of claim 21, wherein the purity of said polyalkylene oxide carboxylic acid is greater than 97%.

23. The method of claim 22, wherein the purity of said polyalkylene oxide carboxylic acid is greater than 99%.

* * * * *

UNITED STATES PATENT AND TRADEMARK OFFICE
CERTIFICATE OF CORRECTION

PATENT NO. : 5,605,976
DATED : February 25, 1997
INVENTOR(S) : Martinez et al.

It is certified that error appears in the above-identified patent and that said Letters Patent is hereby corrected as shown below:

Column 2, line 66 "remit" should read --result--;

Column 3, line 63 "carded" should read --carried--;

Column 4, line 64 "carded" should read --carried--;

Column 6, beginning at line 22 "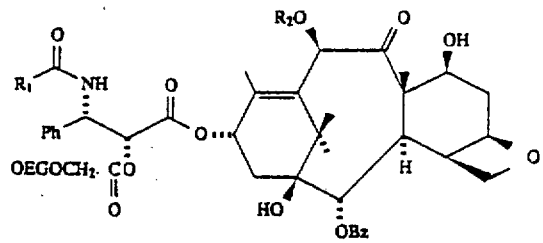"

should read -- 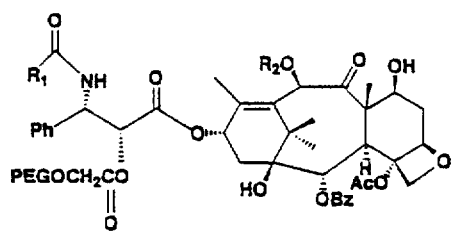 --; and

UNITED STATES PATENT AND TRADEMARK OFFICE
CERTIFICATE OF CORRECTION

PATENT NO. : 5,605,976

DATED : February 25, 1997

INVENTOR(S) : Martinez et al.

It is certified that error appears in the above-indentified patent and that said Letters Patent is hereby corrected as shown below:

Column 8, line 14 "tames" should read --taxanes--.

Signed and Sealed this

Thirteenth Day of May, 1997

*Attest:*

BRUCE LEHMAN

*Attesting Officer*     *Commissioner of Patents and Trademarks*